US010856945B2

(12) United States Patent
Hashimoto et al.

(10) Patent No.: US 10,856,945 B2
(45) Date of Patent: Dec. 8, 2020

(54) INDUSTRIAL ROBOT AND METHOD OF OPERATING THE SAME

(71) Applicant: KAWASAKI JUKOGYO KABUSHIKI KAISHA, Kobe (JP)

(72) Inventors: Yasuhiko Hashimoto, Kobe (JP); Tsuyoshi Maehara, Itami (JP); Masayuki Kamon, Akashi (JP); Shigetsugu Tanaka, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 133 days.

(21) Appl. No.: 15/755,107

(22) PCT Filed: Jun. 24, 2016

(86) PCT No.: PCT/JP2016/003060
§ 371 (c)(1),
(2) Date: Feb. 26, 2018

(87) PCT Pub. No.: WO2017/033376
PCT Pub. Date: Mar. 2, 2017

(65) Prior Publication Data
US 2018/0250831 A1 Sep. 6, 2018

(30) Foreign Application Priority Data

Aug. 25, 2015 (JP) .................................. 2015-165479

(51) Int. Cl.
*B25J 9/16* (2006.01)
*A61B 34/37* (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ......... A61B 34/37; A61B 34/32; A61B 34/35; A61B 34/70; B25J 9/0087; B25J 9/0081;
(Continued)

(56) References Cited

U.S. PATENT DOCUMENTS 6,522,949 B1 2/2003 Ikeda et al.
9,199,372 B2 * 12/2015 Henderson ........... A61B 6/0457
(Continued)

FOREIGN PATENT DOCUMENTS

JP  S59-135507 A  8/1984
JP  S62-49403 A   3/1987
(Continued)

OTHER PUBLICATIONS

Sep. 27, 2016 International Search Report issued in International Patent Application No. PCT/JP2016/003060.
(Continued)

*Primary Examiner* — Masud Ahmed
(74) *Attorney, Agent, or Firm* — Oliff PLC

(57) ABSTRACT

To provide an industrial robot and a method of operating the same which are capable of appropriately handling, when an abnormal state occurs during an automatic operation of the robot, the abnormal state without significantly degrading the work efficiency. The industrial robot includes a robot main body (1) having a robot arm, a robot control device (7) configured to control operation of the robot main body (1) and an abnormal state detecting device (8) configured to detect abnormality in a work state of the robot main body (1). The robot control device (7) includes an automatic operation performing means (9) for controlling the operation of the robot main body (1) to perform an automatic operation based on a given operation program, and an automatic operation correcting means (10) for correcting the operation of the robot main body (1) in the automatic operation based
(Continued)

on a manual control performed by an operator according to a detection result of the abnormal state detecting device (8).

16 Claims, 12 Drawing Sheets

(51) Int. Cl.
*G05B 19/418* (2006.01)
*B25J 9/00* (2006.01)
*B23P 19/04* (2006.01)
*B25J 13/00* (2006.01)
*B25J 19/04* (2006.01)
*B25J 13/08* (2006.01)
*B25J 3/00* (2006.01)
*B25J 13/06* (2006.01)
*B25J 18/00* (2006.01)
*B25J 19/02* (2006.01)
*B25J 3/04* (2006.01)
*B23Q 15/12* (2006.01)
*B25J 13/02* (2006.01)
*B25J 11/00* (2006.01)
*G06F 3/01* (2006.01)
*H04N 5/232* (2006.01)
*H04N 7/18* (2006.01)
*A61B 34/32* (2016.01)
*G06T 7/62* (2017.01)
*G06T 7/70* (2017.01)
*B23P 21/00* (2006.01)

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC ...... B25J 9/1646; B25J 9/1653; B25J 9/1674; B25J 9/1612; B25J 19/028; B25J 9/1602; B25J 13/085; B25J 13/087; B25J 9/0084; B25J 9/1697; B25J 13/006; B25J 13/08; B25J 3/00; B25J 9/1669; B25J 13/06; B25J 13/088; B25J 18/00; B25J 9/161; B25J 9/1664; B25J 9/1682; B25J 9/1689; B25J 19/023; B25J 3/04; B25J 9/1633; B25J 9/1628; B25J 13/02; B25J 9/163; B25J 11/008; B25J 13/003; B25J 13/065; B25J 13/025; B25J 13/084; B25J 13/00; B25J 19/04; B25J 9/126; B25J 19/02; B25J 19/06; B25J 11/005; B25J 9/1661; B25J 9/1692; G05B 19/4182; G05B 2219/37297; G05B 2219/39102; G05B 2219/40143; G05B 2219/39004; G05B 2219/40182; G05B 2219/40145; G05B 2219/40387; G05B 2219/40139; G05B 2219/40161; G05B 2219/40146; G05B 2219/40627; G05B 2219/39439; G05B 2219/40022; G05B 2219/39531; G05B 2219/40163; G05B 2219/39533; G05B 2219/35464; G05B 2219/40142; G05B 2219/33007; G05B 2219/40169; G05B 2219/40183; G05B 2219/40134; G05B 2219/40195; G05B 2219/40162; G05B 2219/40136; G06T 7/62; G06T 7/70; B23Q 15/12; G06F 3/017; H04N 5/23219; H04N 7/181; B23P 19/04; B23P 21/002; B23P 21/00; Y10S 901/09; Y10S 901/47; Y10S 901/08; Y10S 901/03; Y10S 901/27; Y10S 901/41; Y10S 901/10; Y10S 901/46; Y10S 901/02; Y02P 90/02

See application file for complete search history.

(56) References Cited

U.S. PATENT DOCUMENTS

| | | | | |
|---|---|---|---|---|
| 10,292,887 B2* | 5/2019 | Kang | .............. | A61B 34/30 |
| 2005/0234327 A1* | 10/2005 | Saracen | .............. | A61B 6/0457 |
| | | | | 600/407 |
| 2012/0002216 A1* | 1/2012 | Shibata | .............. | H01L 21/681 |
| | | | | 356/614 |
| 2013/0006423 A1* | 1/2013 | Ito | .............. | B25J 9/1612 |
| | | | | 700/259 |
| 2013/0238124 A1* | 9/2013 | Suzuki | .............. | B25J 9/16 |
| | | | | 700/250 |
| 2014/0379128 A1* | 12/2014 | Ishikawa | .............. | B25J 9/1674 |
| | | | | 700/250 |
| 2015/0005936 A1* | 1/2015 | Ito | .............. | B25J 9/163 |
| | | | | 700/250 |

(56) References Cited

U.S. PATENT DOCUMENTS

2015/0127151 A1 5/2015 Riedel et al.
2017/0341240 A1* 11/2017 Nakaya .................. G05B 9/02

FOREIGN PATENT DOCUMENTS

| JP | S62-154009 A | 7/1987 |
|----|---|---|
| JP | S63-106007 A | 5/1988 |
| JP | S64-34686 A | 2/1989 |
| JP | H08-85043 A | 4/1996 |
| JP | H09-305209 A | 11/1997 |
| JP | 2003-311661 A | 11/2003 |
| JP | 2011-224696 A | 11/2011 |
| JP | 2013-071231 A | 4/2013 |
| JP | 2016-083713 A | 5/2016 |
| TW | 201623123 A | 7/2016 |

OTHER PUBLICATIONS

Feb. 27, 2018 International Preliminary Report on Patentability issued in International Patent Application No. PCT/JP2016/003060.
Jun. 19, 2017 Office Action issued in Taiwanese Patent Application No. 105124425.

* cited by examiner

INDUSTRIAL ROBOT AND METHOD OF OPERATING THE SAME

TECHNICAL FIELD

The present disclosure relates to an industrial robot and a method of operating the same in which conveying and assembling works, etc. of workpieces are performed.

BACKGROUND ART

Conventionally, industrial robots are installed in various production plants of electric devices, machines, automobiles, etc. as conveying robots for conveying workpieces or as work robots for processing workpieces, etc.

In a case of repeating the same work using the industrial robot, there is an operating method for pre-programming operation of the robot so that the robot is operated by an automatic operation based on the given operation program. According to this operating method, it is possible to improve work efficiency without requiring a manual control of the robot by the operator.

Meanwhile, even when repeating the same work using the industrial robot, an obstacle which did not exist in a previous work may appear, or the position or shape of a work target (a structural body to which a workpiece is attached, etc.) may vary from those estimated in advance.

When such a state which is different from an initially estimated state (abnormal state) occurs, operating the robot according to the prepared operation program will cause unintentional interference of the workpiece, which is held by a robot hand, or the robot itself with the obstacle or the work target, or make it impossible to perform a given work (the assembling work of the workpiece etc.).

Therefore, a technique is proposed in which, if the abnormal state occurs during the automatic operation of the robot, the operating mode is switched from an automatic operation mode to a manual operation mode by an operator. For example, a technique described in Patent Document 1 is for imaging a work environment of the robot by a camera, detecting the presence of the abnormal state by using the image, and switching the automatic operation mode to the manual operation mode once the abnormal state is detected.

According to this conventional technique, even if the abnormal state occurs during the automatic operation of the robot, by switching the operating mode of the robot from the automatic operation mode to the manual operation mode, the intentional interference of the workpiece held by the robot hand, etc. with the obstacle is prevented, and it is possible to cause the robot to perform the given work (the assembling work of the workpiece etc.) while avoiding the obstacle.

Note that there is a master-slave manipulator as a representative technique for manually operating the robot. The master-slave manipulator includes a master arm and a slave arm which are communicably connected to each other in a wired or wireless manner, and when an operator manually operates the master arm, this movement is transferred to the slave arm as an instruction value, and thus it is possible to cause the slave arm to make the same movement as the master arm.

Further, in order to make the industrial robot automatically perform the work, the robot is necessary to be taught with information required for the work and store the information therein. A method of teaching the robot includes, for example, direct teaching by a teacher directly touching and moving the robot (e.g., see Patent Document 2), teaching by a remote control using a teaching pendant (e.g., see Patent Document 3), teaching by programming, and teaching by a master slave.

REFERENCE DOCUMENTS OF CONVENTIONAL ART

Patent Documents

[Patent Document 1] JP2003-311661A
[Patent Document 2] JP2013-071231A
[Patent Document 3] JP2016-083713A

DESCRIPTION OF THE DISCLOSURE

Problems to be Solved by the Disclosure

However, the conventional technique described above (Patent Document 1) is for stopping, when the abnormal state is detected by the camera during the automatic operation of the robot, the automatic operation mode and completely switching it to the manual operation mode. Therefore, after the operating mode of the robot is switched to the manual operation mode, the manipulation of the robot becomes entirely up to the operator.

Thus, the prepared operation program cannot be used at all after the operating mode is switched. Therefore, excessive burden falls on the operator and the work efficiency is degraded.

Further, since the conventional technique described above is for detecting the abnormal state by using the image from the camera, it is difficult to ensure sufficient detection accuracy depending on the work environment, and it may be impossible to suitably switch the operating mode.

In addition, since it is necessary to manipulate the robot by the operator's total manual control as described above after the operating mode is switched from the automatic operation to the manual operation, the manual control based on the image information of the camera makes the operator's burden more excessive.

The present disclosure is made in view of the issues of the conventional techniques and has a first purpose to provide an industrial robot and a method of operating the same, which are capable of appropriately responding, even when an abnormal state occurs during an automatic operation of a robot, to the abnormal state without significantly degrading work efficiency.

Further, part of the operation taught to the robot may be necessary to be changed for various reasons. For example, when a work target, a work environment, etc. of the robot are partially changed from those when taught, problems, such as the robot becoming impossible to carry out the objective work, and the work accuracy being lowered, may arise.

Moreover, after finishing the teaching, a fault may be discovered in the initially-created teaching information for part of the work. In such a case, the teaching information to be used for an automatic operation of the robot is changed by again performing the teaching.

Here, in performing the teaching again, when the teaching worker is skillful, the accuracy of the operation of the robot becomes higher by mainly basing on the instruction value inputted from the worker more than the instruction value in the automatic operation, whereas when the worker is not skillful, if mainly based on the instruction value inputted from the worker, the operation accuracy of the robot may rather degrade.

Therefore, a second purpose of the present disclosure is to provide a robot system and a method of controlling the same, which are capable of changing, when correcting a preset operation of a robot, the degree of correction.

That is, the present disclosure aims to solve at least one of a first issue that work efficiency may significantly degrade when an abnormal state occurs during an automatic operation of a robot and a second issue that when performing teaching to the robot again, if a worker is not skillful, mainly basing on an instruction value inputted from the worker may result in rather degrading operation accuracy of the robot.

Summary of the Disclosure

In order to solve the issue, an industrial robot according to 1st aspect of the present disclosure includes a robot main body having a robot arm, a robot control device configured to control operation of the robot main body, and an abnormal state detecting device configured to detect abnormality in a work state of the robot main body. The robot control device includes an automatic operation performing means for controlling the operation of the robot main body to perform an automatic operation based on a given operation program, and an automatic operation correcting means for correcting the operation of the robot main body in the automatic operation based on a manual control performed by an operator according to a detection result of the abnormal state detecting device.

According to 2nd aspect of the present disclosure, in the 1st aspect, an end effector configured to hold a workpiece may be provided to the robot arm, and the given operation program may cause the robot main body to perform a conveying operation in which the workpiece held by the end effector is conveyed from a conveying source to a conveying destination, and an assembling operation in which the workpiece is attached to a target object at the conveying destination.

According to 3rd aspect of the present disclosure, in the 2nd aspect, the abnormal state detecting device may detect abnormality in the work state of the robot main body in the assembling operation.

According to 4th aspect of the present disclosure, in the 3rd aspect, the abnormality in the work state of the robot main body may include occurrence of an unexpected assembling error in the assembling operation.

According to 5th aspect of the present disclosure, in any one of the 1st to 4th aspects, the abnormal state detecting device may have a reaction force detecting means for detecting a reaction force externally acting on the robot main body, and may be configured to provide haptics information to the operator according to a detection result of the reaction force detecting means.

According to 6th aspect of the present disclosure, in any one of the 1st to 5th aspects, the abnormal state detecting device may provide visual information regarding a workspace of the robot main body to the operator.

According to 7th aspect of the present disclosure, in any one of the 1st to 6th aspects, a plurality of robot main bodies may be provided, and a correction target selecting means for selecting the robot main body of which operation is corrected by the automatic operation correcting means, from the plurality of robot main bodies may further be included.

According to 8th aspect of the present disclosure, in any one of the 1st to 7th aspects, when an operational instruction for the robot main body in the automatic operation is $\Delta P1$, an operational instruction for the robot main body in the manual control is $\Delta P2$, and a correction coefficient is $\alpha$ ($0 \le \alpha \le 1$), the automatic operation correcting means may be configured to generate an operational instruction $\Delta P0$ to be given to the robot main body based on the following equation:

$$\Delta P0 = (1-\alpha) \times \Delta P1 + \alpha \times \Delta P2.$$

According to 9th aspect of the present disclosure, in the 8th aspect, the automatic operation correcting means may have a correction coefficient adjusting means for adjusting the correction coefficient.

According to 10th aspect of the present disclosure, in any one of the 1st to 9th aspects, the robot control device may have a learning function achieving means for correcting the operation of the automatic operation based on a history of correcting the operation in the automatic operation by the automatic operation correcting means.

According to 11th aspect of the present disclosure, a robot main body having a robot arm, a manipulator configured to receive a manipulating instruction from an operator, a storage device storing a task program for causing the robot main body to perform a given operation, and a robot control device configured to control the operation of the robot main body, are provided. The robot control device includes an automatic operation performing means for controlling the operation of the robot main body to perform an automatic operation based on the task program, and an automatic operation correcting means for correcting, when an operational instruction is inputted from the manipulator during the automatic operation, by having an operational instruction for the robot main body in the automatic operation $\Delta P1$ and an operational instruction for the robot main body in the manual control $\Delta P2$, the operation of the robot main body in the automatic operation by giving a sum of a value obtained by multiplying $\Delta P1$ by a first coefficient A and a value obtained by multiplying $\Delta P2$ by a second coefficient B to the robot main body.

According to 12th aspect of the present disclosure, in the 11th aspect, the first coefficient A and the second coefficient B may be associated with each other so that when one of the coefficients increases, the other coefficient decreases.

According to 13th aspect of the present disclosure, in the 11th or 12th aspect, the first coefficient A and the second coefficient B may be such coefficients that a value obtained by multiplying the first coefficient A and the second coefficient B becomes a first given preset value.

According to 14th aspect of the present disclosure, in the 11th or 12th aspect, the first coefficient A and the second coefficient B may be such coefficients that a value obtained by adding the first coefficient A and the second coefficient B on each other becomes a second given preset value.

According to 15th aspect of the present disclosure, in any one of the 11th to 14th aspects, the second coefficient B may be a variable that becomes a preset value over a given period of time since the operational instruction is inputted from the manipulator.

According to 16th aspect of the present disclosure, in any one of the 11th to 15th aspects, an adjusting means for adjusting the second coefficient B, may further be provided.

According to 17th aspect of the present disclosure, a method of operating an industrial robot including a robot main body having a robot arm, a robot control device configured to control operation of the robot main body, and an abnormal state detecting device configured to detect abnormality in a work state of the robot main body is provided. The method includes an automatic operation performing process in which the robot control device is used to control the operation of the robot main body to perform an automatic operation based on a given operation program, and an automatic operation correcting process in which the operation of the robot main body in the automatic operation is corrected based on a manual control performed by an operator according to a detection result of the abnormal state detecting device.

According to 18th aspect of the present disclosure, in the 17th aspect, an end effector configured to hold a workpiece may be provided to the robot arm, and the given operation program may cause the robot main body to perform a conveying operation in which the workpiece held by the end effector is conveyed from a conveying source to a conveying destination, and an assembling operation in which the workpiece is attached to a target object at the conveying destination.

According to 19th aspect of the present disclosure, in the 18th aspect, the abnormal state detecting device may be used to detect abnormality in the work state of the robot main body in the assembling operation.

According to 20th aspect of the present disclosure, in the 19th aspect, the abnormality in the work state of the robot main body may include occurrence of an unexpected assembling error in the assembling operation.

According to 21st aspect of the present disclosure, in any one of the 17th to 20th aspects, the abnormal state detecting device may have a reaction force detecting means for detecting a reaction force externally acting on the robot main body, and the abnormal state detecting device may be used to provide haptics information to the operator according to a detection result of the reaction force detecting means.

According to 22nd aspect of the present disclosure, in any one of the 17th to 21st aspects, the abnormal state detecting device may be used to provide visual information regarding a workspace of the robot main body to the operator.

According to 23rd aspect of the present disclosure, in any one of the 17th to 22nd aspects, a correction target selecting process in which the robot main body of which operation is corrected by the automatic operation correcting process is selected from a plurality of robot main bodies, may further be provided.

According to 24th aspect of the present disclosure, in any one of the 17th to 23rd aspects, in the automatic operation correcting process, when an operational instruction for the robot main body in the automatic operation is $\Delta P1$, an operational instruction for the robot main body in the manual control is $\Delta P2$, and a correction coefficient is $\alpha$ ($0 \leq \alpha \leq 1$), an operational instruction $\Delta P0$ to be given to the robot main body may be generated based on the following equation:

$$\Delta P0 = (1-\alpha) \times \Delta P1 + \alpha \times \Delta P2.$$

According to 25th aspect of the present disclosure, in the 24th aspect, the automatic operation correcting process may include a correction coefficient adjusting process in which the correction coefficient is adjusted.

According to 26th aspect of the present disclosure, in any one of the 17th to 25th aspects, in the automatic operation correcting process, the operation of the automatic operation may be corrected based on a history of correcting the operation in the automatic operation.

According to 27th aspect of the present disclosure, an method of operating an industrial robot including a robot main body, a manipulator configured to receive a manipulating instruction from an operator, and a storage device storing a task program for causing the robot main body to perform a given operation is provided. The method includes (A) executing an automatic operation of the robot main body based on the task program, and (B) correcting, when an operational instruction is inputted from the manipulator during the executing (A), by having an operational instruction for the robot main body in the automatic operation $\Delta P1$ and an operational instruction for the robot main body in the manual control $\Delta P2$, the operation of the robot main body in the automatic operation by giving a sum of a value obtained by multiplying $\Delta P1$ by a first coefficient A and a value obtained by multiplying $\Delta P2$ by a second coefficient B to the robot main body.

According to 28th aspect of the present disclosure, in the 27th aspect, the first coefficient A and the second coefficient B may be associated with each other so that when one of the coefficients increases, the other coefficient decreases.

According to 29th aspect of the present disclosure, in the 27th or 28th aspect, the first coefficient A and the second coefficient B may be such coefficients that a value obtained by multiplying the first coefficient A and the second coefficient B becomes a first given preset value.

According to 30th aspect of the present disclosure, in the 27th or 28th aspect, the first coefficient A and the second coefficient B may be such coefficients that a value obtained by adding the first coefficient A and the second coefficient B on each other becomes a second given preset value.

According to 31st aspect of the present disclosure, in any one of the 27th to 30th aspects, the second coefficient B may be a variable that becomes a preset value over a given period of time since the operational instruction is inputted from the manipulator.

According to 32nd aspect of the present disclosure, in any one of the 27th to 31st aspects, the industrial robot may further include an adjusting means for adjusting the second coefficient B.

Effects of the Disclosure

According to the present disclosure with the above configuration, the industrial robot and the method of operating the same which are capable of appropriately handling, when an abnormal state occurs during the automatic operation of the robot, the abnormal state without significantly degrading the work efficiency, can be provided.

Further, according to the present disclosure with the above configuration, the industrial robot and the method of operating the same which are capable of changing, when correcting a preset operation of the robot, the degree of correction, can be provided.

MODES FOR CARRYING OUT THE DISCLOSURE

First Embodiment

Hereinafter, an industrial robot and a method of operating the same according to a first embodiment will be described with reference to the drawings.

[Configuration of Industrial Robot]

Figure 1:
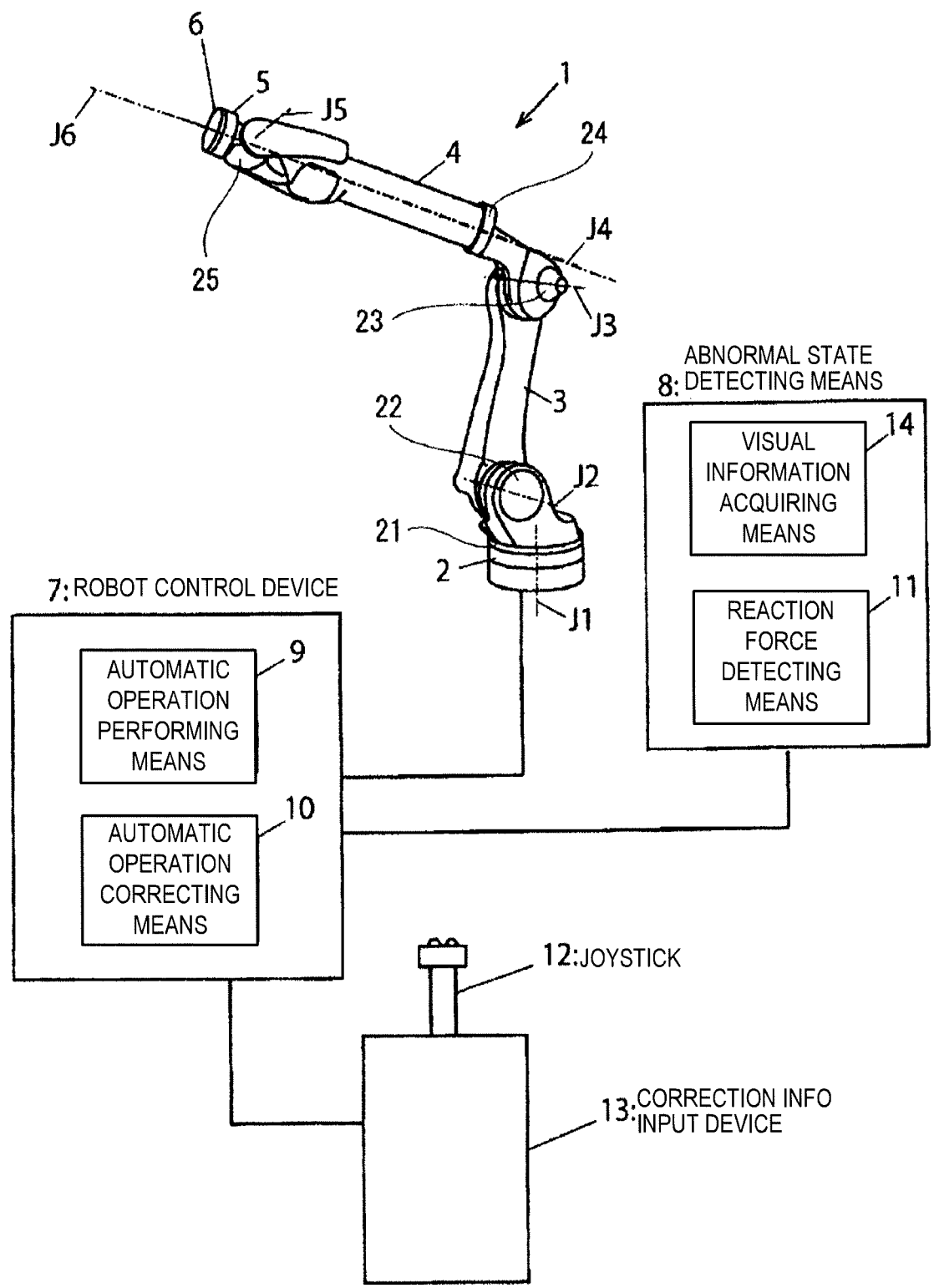
FIG. 1 is a schematic diagram illustrating a schematic configuration of an industrial robot according to one embodiment of the present disclosure.

As illustrated in FIG. 1, a robot main body 1 of the industrial robot according to this embodiment has a pedestal 2 rotatable around a first axis (rotation axis) J1 via a first joint part 21, and a base end of a lower arm 3 is connected to this pedestal 2 via a second joint part 22 to be rotatable around a second axis J2. A base end of an upper arm 4 is connected to a tip end of the lower arm 3 via a third joint part 23 to be rotatable around a third axis J3.

The upper arm 4 is rotatable around its longitudinal axis (fourth axis) J4 via a fourth joint part 24. A wrist part 5 is connected to a tip end of the upper arm 4 via a fifth joint part 25 to be swingable around a fifth axis (swinging axis) J5. The fifth axis J5 is orthogonal to the longitudinal axis (fourth axis) J4 of the upper arm 4.

A tip end surface of the wrist part 5 is provided with a rotary body 6 rotatable around a center axis (sixth axis) J6 of the wrist part 5. An end effector (not illustrated) capable of holding a workpiece is attached to the rotary body 6.

Figure 5:
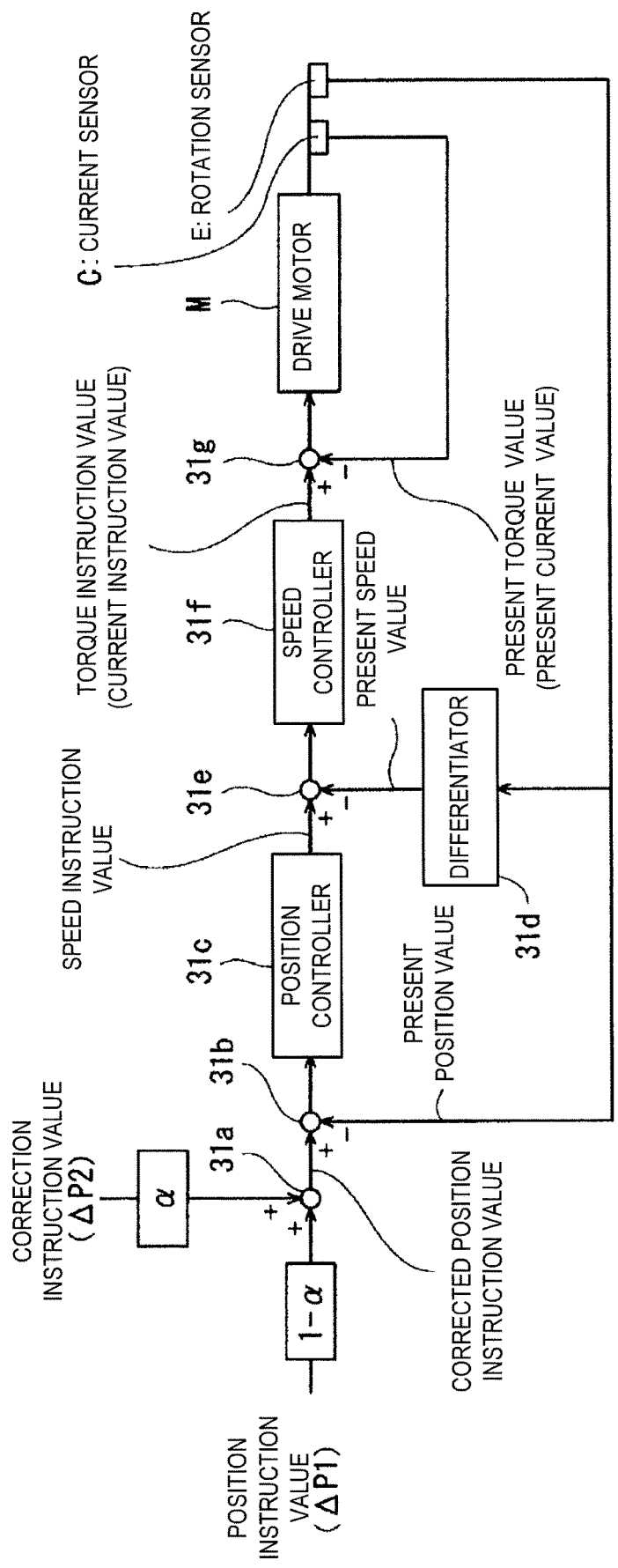
FIG. 5 is a block diagram illustrating one example of a control system of an automatic operation correcting means illustrated in FIG. 1.

Each of the first joint part 21 to the fifth joint part 25 and the rotary body 6 is provided with a drive motor M as one example of an actuator for relatively rotating two coupled members to each other (see FIG. 5). The drive motor M may be, for example, a servo motor which is servo-controlled by a robot control device 7. Moreover, each of the first joint part 21 to the fifth joint part 25 and the rotary body 6 is provided with a rotation sensor E for detecting a rotational position of the drive motor M (see FIG. 5) and a current sensor C for detecting current which controls the rotation of the drive motor M (see FIG. 5). The rotation sensor E may be, for example, an encoder.

The pedestal 2, the lower arm 3, the upper arm 4, the wrist part 5, the rotary body 6, and the end effector constitute the robot main body 1 of the industrial robot.

The industrial robot according to this embodiment includes the robot control device 7 for controlling the operation of the robot main body 1. Furthermore, the industrial robot includes an abnormal state detecting device 8 for detecting abnormality in a work state of the robot main body 1.

The robot control device 7 has an automatic operation performing means 9 for controlling the operation of the robot main body 1 to perform an automatic operation based on a given operation program prepared in advance. This given operation program is for causing the robot main body 1 to execute a conveying operation in which the workpiece held by the end effector is conveyed from a conveying source to a conveying destination and an assembling operation in which the workpiece is attached to a target object at the conveying destination.

Note that the robot control device 7 may be comprised of, for example, an arithmetic part (not illustrated), such as a microcontroller, an MPU and a PLC (Programmable Logic Controller), a logic circuit, etc., and a memory part (not illustrated), such as a ROM or a RAM. Further the robot control device 7 may not only be in a form comprised of a single control device, but also in a form comprised of a group of control devices in which a plurality of control devices collaborate with each other to execute the control of the robot main body 1 (industrial robot).

The robot control device 7 further includes an automatic operation correcting means 10 for correcting the operation of the robot main body 1 in the automatic operation based on a manual control performed by an operator according to the detection result of the abnormal state detecting device 8. The abnormal state detecting device 8 described above is for detecting abnormality in the work state of the robot main body 1 in the assembling operation of the workpiece to the target object.

The abnormality in the work state of the robot main body 1 detected by the abnormal state detecting device 8 corresponds to occurrence of an unexpected assembling error in the assembling operation of the workpiece to the target object. The abnormal state detecting device 8 has a reaction force detecting means 11 for detecting a reaction force externally acting on the robot main body 1, and is configured to provide force and tactile information (haptics information) to the operator according to the detection result of the reaction force detecting means 11.

For example, when the installation position of the target object is deviated from a normal position in the assembling operation of the workpiece to the target object, a spatial relationship between the workpiece and the target object varies from a spatial relationship as a condition of a given operation program. Therefore, if the workpiece is to be moved and assembled with the target object based on the given operation program, an assembling part of the workpiece and an assembled part of the target object are not properly positioned, and an unexpected assembling error occurs.

When such an unexpected assembling error occurs, since an unexpected reaction force acts on the workpiece from the target object, this reaction force is detected by the reaction force detecting means 11. More specifically, the reaction force transmitted to a robot arm via the workpiece is detected by using the reaction force detecting means 11.

The reaction force detecting means 11 may adopt, for example, a force reflection type system or a force feedback type system used for bilateral control of a master-slave manipulator.

The industrial robot according to this embodiment further includes a correction information input device 13 having a manual control input device, for example, a joystick 12. As the manual control input device, other than the joystick, for example, a master arm having a similar structure to a robot arm (slave arm) may be used. The correction information input device 13 and the robot control device 7 are communicably connected in a wired or wireless manner.

According to the detection result of the reaction force detecting means 11, the joystick 12 of the correction information input device 13 is caused to perform a tilting motion, and force and tactile senses are provided to the operator through this tilting motion. For example, when the assembling part of the workpiece and the assembled part of the target object are not properly positioned and the unexpected assembling error occurs, the reaction force thus acting on the workpiece and the robot arm is detected by the reaction force detecting means 11, and the detection result is transmitted to the operator as force and tactile senses through the tilting motion of the joystick 12.

Moreover, the abnormal state detecting device 8 may include, alternatively to or in addition to the reaction force detecting means 11 described above, a visual information acquiring means 14 for providing visual information regarding a workspace of the robot main body 1 to the operator. Specifically, the visual information acquiring means 14 may be comprised of an imaging means (e.g., a camera) for imaging the workspace of the robot main body 1. The imaging means may be provided in the robot arm or the end effector.

[Operation and Effect of Industrial Robot]

Next, a method of operating the industrial robot according to the first embodiment will be described with reference to FIGS. 2 to 5. Note that, the following operation is executed by an arithmetic part of the robot control device 7 reading a program stored in a memory part of the robot control device 7 or a storage device (see FIG. 8).

Further, in this specification, the control mode in which the robot main body 1 operates in accordance with a preset task program is referred to as "automatic operation mode." In the automatic operation mode, similar to a conventional teaching playback robot, the robot main body 1 automatically performs a given operation without the operator manipulating the joystick 12.

Moreover, in this specification, the control mode in which the robot main body 1 operates based on the operation of the operator received by the joystick 12 is referred to as "manual operation mode." Note that, in the manual operation mode, the robot main body 1 may be operated so as to completely follow a manipulating instruction received from the joystick 12, or the robot main body 1 may be operated while correcting the manipulating instruction received from the joystick 12 with a preset program (e.g., hand shake correction).

Furthermore, in this specification, the control mode in which the robot main body 1 operating according to the preset task program is corrected with the operation of the operator received by the joystick 12 is referred to as "operation correcting mode."

Figure 2:
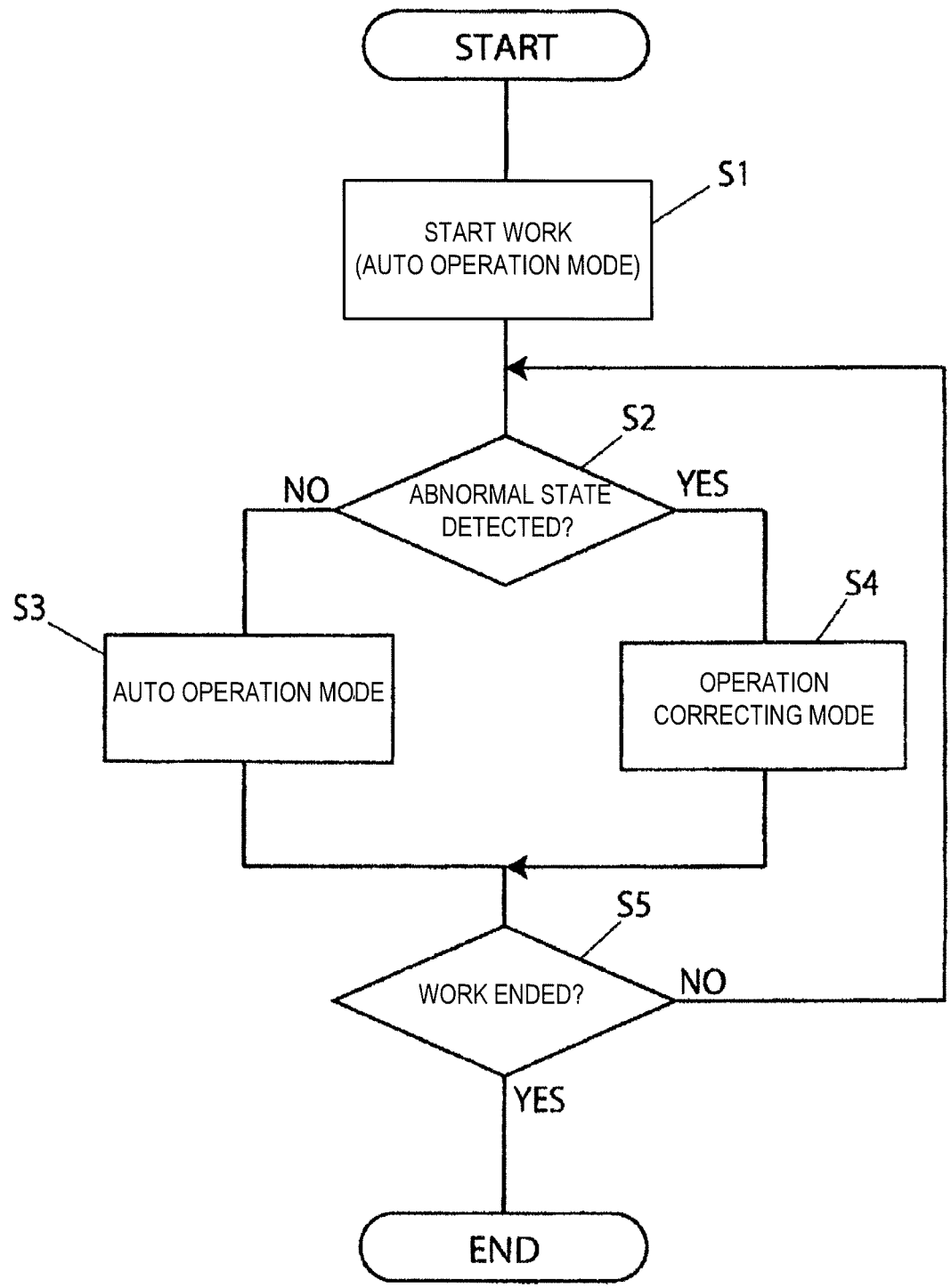
FIG. 2 is a flowchart illustrating a method of operating the industrial robot illustrated in FIG. 1.

When conveying the workpiece and attaching it to the target object by using the industrial robot illustrated in FIG. 1, first, the robot control device 7 is used to control the operation of the robot main body 1 to perform the automatic operation based on a given operation program (automatic operation performing process). That is, as illustrated in FIG. 2, the workpiece conveying and assembling works are started in the automatic operation mode (Step S1).

If no abnormality of the work state is detected by the abnormal state detecting device 8 after the workpiece conveying and assembling works are started (Step S2), the automatic operation mode is continued as it is (Step S3), the workpiece is conveyed from the conveying source to the conveying destination, the workpiece is assembled to the target object at the conveying destination, and the work is ended (Step S5). In this case, the manual control by the operator is not performed from the start to the end of the workpiece conveying and assembling works, and the correction of the automatic operation by the automatic operation correcting means 10 is not performed.

On the other hand, when abnormality in the work state is detected by the abnormal state detecting device 8 (Step S2), the detection result is transmitted to the operator. For example, in the assembling operation of the workpiece to the target object, if the workpiece and the target object are not properly positioned and an unexpected reaction force is generated between them, the reaction force detecting means 11 causes the tilting motion to the joystick 12 according to this reaction force, and force and tactile senses are provided to the operator holding the joystick 12.

Sensing the force and tactile senses, the operator manipulates the joystick 12 based on the force and tactile senses, and the automatic operation of the robot main body 1 is corrected by this manual control (automatic operation correcting process). The operating mode in this automatic operation correcting process is referred to as the operation correcting mode S4.

Further, in a case of providing the visual information regarding the workspace of the robot main body 1 by using the visual information acquiring means 14 comprised of the imaging means, such as the camera, the operator determines whether the abnormality has occurred based on the provided visual information. Then, upon confirming the occurrence of the abnormality, the operator manipulates the joystick 12 to correct the operation of the robot main body 1 in the automatic operation (operation correcting mode S4).

For example, in the assembling operation of the workpiece to the target object, if the positioning of the assembling part of the workpiece to the assembled part of the target object is determined to be improper based on the visual information, the operator manipulates the joystick 12 to correct the operation of the robot main body 1 in the automatic operation (operation correcting mode S4).

While the workpiece conveying and assembling works are continued in the operation correcting mode S4, whether the abnormal state is detected is determined (Step S2), and if the abnormal state is resolved, the operation correcting mode S4 is switched to the automatic operation mode S3.

Figure 3:
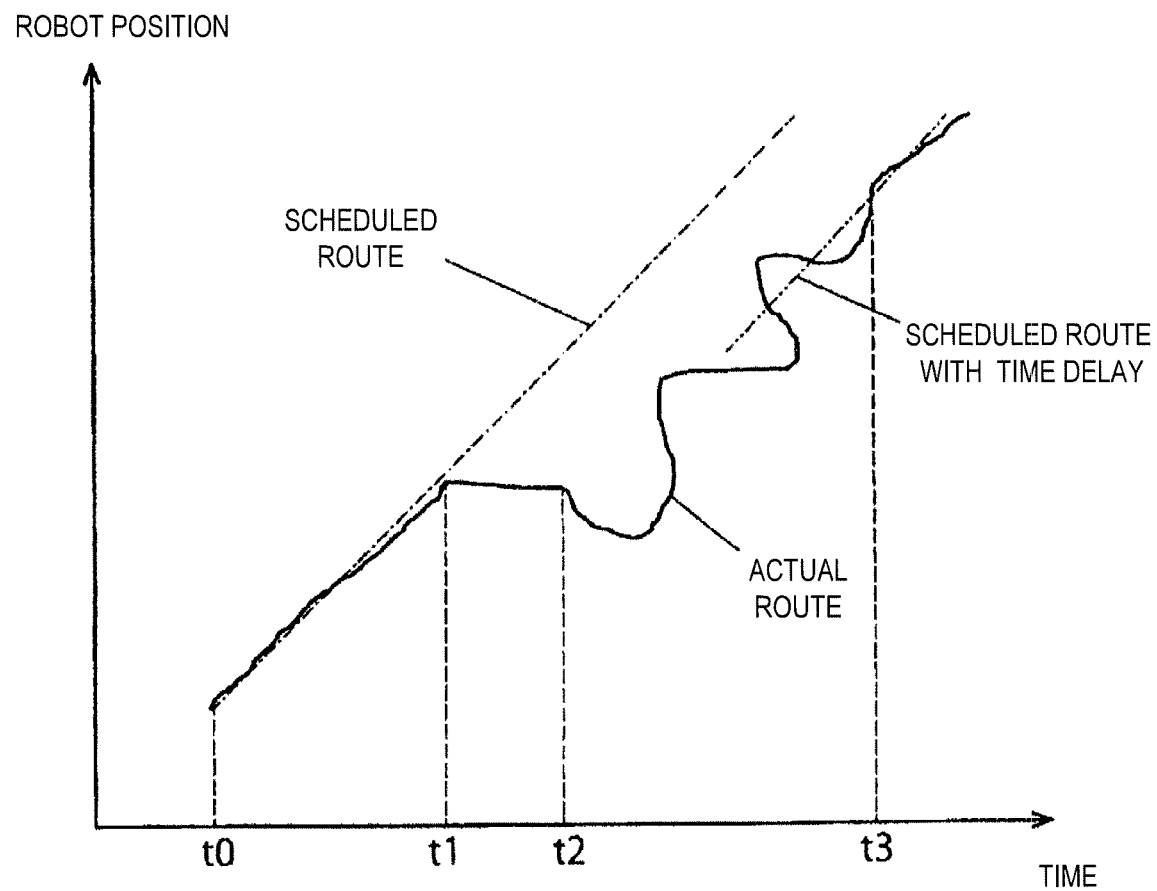
FIG. 3 is a chart illustrating a graph relating to a temporal change in the position of the industrial robot illustrated in FIG. 1.

FIG. 3 is a chart illustrating one example of a graph of a temporal change in the robot position in the workpiece conveying and assembling works. FIGS. 4A to 4E are diagrams illustrating the spatial relationship between the workpiece W held by the end effector 15 and the target object O to which the workpiece W is attached, at each time point.

Figure 4A:
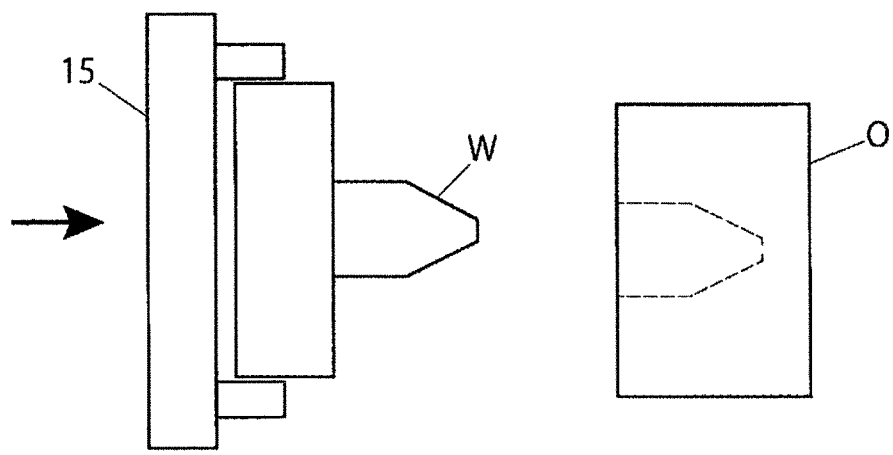
FIG. 4A is a schematic diagram illustrating workpiece conveying and assembling operations of the industrial robot illustrated in FIG. 1.

As illustrated in FIG. 3, when the workpiece conveying and assembling works are started in the automatic operation mode at time t0 (Step S1), the robot main body 1 is driven based on the given program, and the robot position changes along a given pre-registered route (scheduled route). The state of this time is illustrated in FIG. 4A.

Here, in the conveying operation in which the workpiece W is conveyed from the conveying source to the conveying destination, the possibility of the abnormal state occurring during this is low, and the conveying operation has a high possibility of completing by only the automatic operation. On the other hand, in the attaching operation in which the workpiece W is attached to the target object O at the conveying destination, there is a possibility that the abnormal state occurs due to a positional deviation in the disposition of the target object O etc.

Figure 4B:
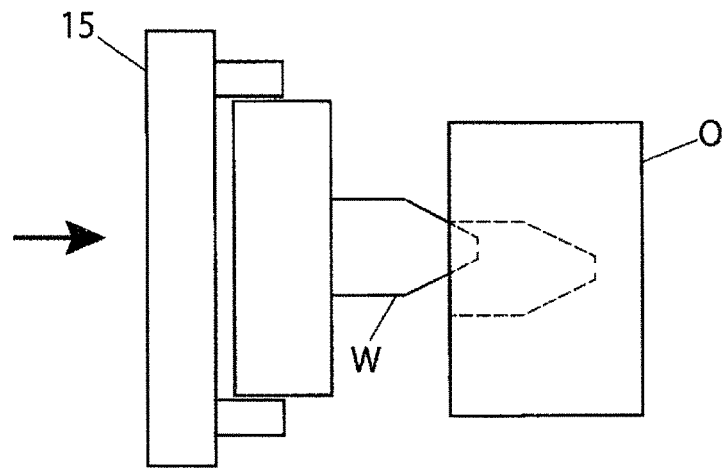
FIG. 4B is another schematic diagram illustrating the workpiece conveying and assembling operations of the industrial robot illustrated in FIG. 1.

In the example illustrated in FIG. 3, at time t1, due to some sort of reason (e.g., interference between the workpiece W and the target object O illustrated in FIG. 4B), the robot main body 1 stops moving as scheduled (the abnormal state occurred). That is, the actual route of the robot position deviates from a given route of the automatic operation. Here, force and tactile senses based on the reaction force acting on the workpiece W and/or the robot main body 1 is transmitted to the operator via the joystick 12 by the reaction force detecting means 11.

Figure 4C:
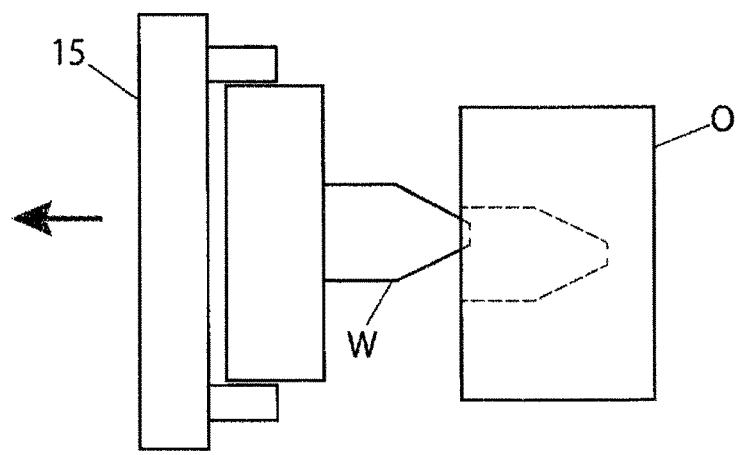
FIG. 4C is another schematic diagram illustrating workpiece conveying and assembling operations of the industrial robot illustrated in FIG. 1.

In response to this, from time t2, the operator manipulates the joystick 12 to cause the end effector 15 of the robot main body 1 to retreat once. The state at this time is illustrated in FIG. 4C. Then, the operation process of the robot main body 1 is progressed while correcting the automatic operation of the robot main body 1 based on the force and tactile senses transmitted from the joystick 12.

Figure 4D:
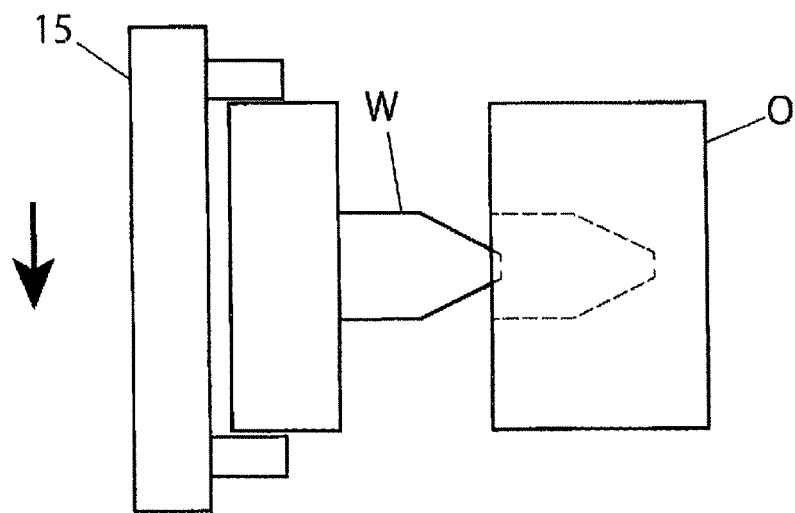
FIG. 4D is another schematic diagram illustrating the workpiece conveying and assembling operations of the industrial robot illustrated in FIG. 1.

As illustrated in FIG. 3, the correction amount by the manual control using the joystick 12 gradually decreases, and the change of the robot position (actual route) approaches the given route (scheduled route with a time delay) of the automatic operation. The state at this time is illustrated in FIG. 4D. When the change in the robot position resumes to the given route (scheduled route with a time delay) of the automatic operation, the unexpected reaction force no longer acts on the workpiece W and/or the robot main body 1 and the force and tactile senses transmitted to the operator via the joystick 12 disappear.

Figure 4E:
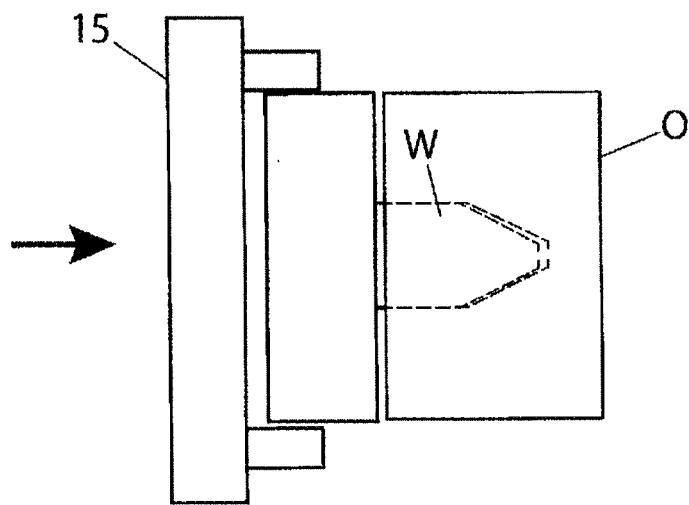
FIG. 4E is another schematic diagram illustrating the workpiece conveying and assembling operations of the industrial robot illustrated in FIG. 1.

In this state, it is unnecessary to correct the automatic operation by the operator's manual control, the robot main body 1 is driven based only on the given automatic operation with no correction, and the given workpiece assembling operation is executed with a time delay. The state at this time is illustrated in FIG. 4E.

Hereinafter, the operation correcting mode described above will be supplementarily described.

To conceptually describe the contents of the operation correcting mode, the operation correcting mode may be such that an operational instruction in the manual control (e.g., minus 10) is superimposed on an operational instruction in the automatic operation (e.g., plus 5) so that the robot performs the corrected operation (minus 5).

Further, in the operation correcting mode, the operation as illustrated in FIG. 5 may be performed. Here, FIG. 5 is a block diagram illustrating one example of a control system of the automatic operation correcting means illustrated in FIG. 1. Note that, in the example illustrated in FIG. 5, when the operational instruction for the robot in the automatic operation is ΔP1 and the operational instruction for the robot in the manual control is ΔP2, ΔP1 and ΔP2 are route instruction values (position instruction values) including time series data. Moreover, in the example illustrated in FIG. 5, for example, an operational instruction ΔP0 given to the robot may be corrected as follows.

$$\Delta P0 = (1-\alpha) \times \Delta P1 + \alpha \times \Delta P2 \qquad \text{Equation (1)}$$

Here, α is a correction coefficient. Note that, when α=0, an instruction for a normal automatic operation is sent, when α=1, it becomes the instruction for a complete remote control operation, and when 0<α<1, it is an operation for an intermediate state therebetween, that is, the operation of the robot main body 1 in the operation correcting mode.

Hereinafter, one example of the operation correcting mode will be described in detail with reference to FIG. 5.

As illustrated in FIG. 5, the automatic operation correcting means 10 includes an adder 31a, subtractors 31b, 31e and 31g, a position controller 31c, a differentiator 31d, and a speed controller 31f, and controls the rotational position of the drive motor M of the robot main body 1 in response to the operational instruction for the robot in the automatic operation (ΔP1) and the operational instruction for the robot in the manual control (ΔP2).

The adder 31a adds ΔP2 to ΔP1 to generate a corrected position instruction value. Here, the adder 31a generates the position instruction value according to the above Equation (1). That is, the adder 31a generates, as the corrected position instruction value, the sum of a value obtained by multiplying the operational instruction for the robot in the automatic operation (ΔP1) by 1−α and a value obtained by multiplying the operational instruction for the robot in the manual control (ΔP2) by α. Then, the adder 31a sends the corrected position instruction value to the subtractor 31b.

Note that the correction coefficient α may be inputted to the automatic operation correcting means 10 by providing a volume knob (correction coefficient adjusting means) to the joystick 12 or the correction information input device 13 and the operator manually adjusting the volume knob. Further, as the correction coefficient adjusting means, for example, a program for causing α to be 0 at a great distance from the work target (a structural body to which the workpiece is attached, etc.), and gradually become close to 1 as approaching the work target may be stored in advance in the storage device (not illustrated). Alternatively, as the correction coefficient adjusting means, a program for causing a to normally be 0 and, when a force-and-tactile sensing part attached to the tip end of the robot main body 1 senses the contact of the workpiece, notifying it to the operator, and switching it to α=1 may be stored in advance in the storage device.

The subtractor 31b subtracts a present position value detected by the rotation sensor E from the corrected position instruction value to generate an angle deviation. The subtractor 31b outputs the generated angle deviation to the position controller 31c.

The position controller 31c generates a speed instruction value from the angular deviation inputted from the subtractor 31b by arithmetic processing based on a predetermined transfer function or proportional coefficient. The position controller 31c outputs the generated speed instruction value to the subtractor 31e.

The differentiator 31d differentiates the present position value information detected by the rotation sensor E to generate a change amount of the rotation angle of the drive motor M per unit time, that is, the present speed value. The differentiator 31d outputs the generated present speed value to the subtractor 31e.

The subtractor 31e subtracts the present speed value inputted from the differentiator 31d from the speed instruction value inputted from the position controller 31c to generate a speed deviation. The subtractor 31e outputs the generated speed deviation to the speed controller 31f.

The speed controller 31f generates a torque instruction value (current instruction value) from the speed deviation inputted from the subtractor 31e by arithmetic processing based on a predetermined transfer function or proportional coefficient. The speed controller 31f outputs the generated torque instruction value to the subtractor 31g.

The subtractor 31g subtracts a present current value detected by the current sensor C from the torque instruction value inputted from the speed controller 31f to generate a current deviation. The subtractor 31g outputs the generated current deviation to the drive motor M to drive the drive motor M.

Thus, the automatic operation correcting means 10 controls the drive motor M so that the robot main body 1 is controlled to perform operation corrected from the operation relating to the automatic operation information.

Note that, in the first embodiment, the form in which the operational instruction for the robot in the manual control ($\Delta P2$) is the route instruction value (position instruction value) including the time series data is adopted, but the present disclosure is not limited to this. For example, a form in which $\Delta P2$ is the speed instruction value may be adopted, or a form in which $\Delta P2$ is the torque instruction value may be adopted.

When $\Delta P2$ is the speed instruction value, a value obtained by multiplying the speed instruction value as $\Delta P2$ by $\alpha$ (manual speed instruction value) is inputted to the subtractor 31e. Further, the subtractor 31e is supplied with a value which the position controller 31c obtains by multiplying the speed instruction value generated based on the operational instruction for the robot in the automatic operation ($\Delta P1$; position instruction value) by $1-\alpha$ (corrected speed instruction value). Furthermore, the subtractor 31e is supplied with the present speed value generated by the differentiator 31d from this differentiator 31d.

Then, the subtractor 31e adds the corrected speed instruction value to the inputted manual speed instruction value and generates the speed deviation based on the value obtained by subtracting the present speed value. Note that the operation after the subtractor 31e generates the speed deviation is executed in the similar manner to that described above.

Similarly, when $\Delta P2$ is the torque instruction value, a value obtained by multiplying the torque instruction value as $\Delta P2$ by $\alpha$ (manual torque instruction value) is inputted to the subtractor 31g. Further, the subtractor 31g is supplied with a value obtained by multiplying the torque instruction value generated by the speed controller 31f by $1-\alpha$ based on the speed deviation inputted from the speed controller 31f via the position controller 31c and the subtractor 31e in response to the operational instruction for the robot in the automatic operation ($\Delta P1$; position instruction value) (corrected torque instruction value). Furthermore, the subtractor 31g is supplied with the present current value detected by the current sensor C.

Then, the subtractor 31g adds the corrected torque instruction value to the inputted manual torque instruction value and subtracts the present current value to generate the current deviation. The subtractor 31g sends the generated current deviation to the drive motor M to drive the drive motor M.

Note that, as another example of the operation correcting mode, for example, if fitting of the present workpiece is actually successful with $\Delta P0$ despite of the automatic operation instruction value $\Delta P1$, when assembling the same workpiece next time, $\Delta P0$ may replace $\Delta P1$ or $\Delta P1$ may be modified to be close to it instead of completely replacing it.

Further, a function for logging $\Delta P2$ and the force-and-tactile information of the robot main body 1 and learning how much and when to correct (learning function achieving means) may be provided to the robot control device 7 to automatically correct the operational instruction in automatic operation $\Delta P1$, opportunities for the remote operator to intervene gradually decrease, and it is possible to achieve the assembling work only by the automatic operation.

As described above, according to the industrial robot and the method of operating the same according to the first embodiment, even when the abnormal state occurs during the automatic operation of the robot, it is possible to correct the automatic operation by the operator's manual control while having the automatic operation as the base of the robot operation. Therefore, it is possible to appropriately handle the abnormal state without significantly degrading the work efficiency.

In addition, if the robot operation (actual route) resumes to the given operation in the automatic operation by the operator's manual control, by suspending the correction on the automatic operation, the automatic operation continues thereafter. Therefore, no special switching mechanism etc. for resuming from the manual operation to the automatic operation is required.

[First Modification]

Figure 6:
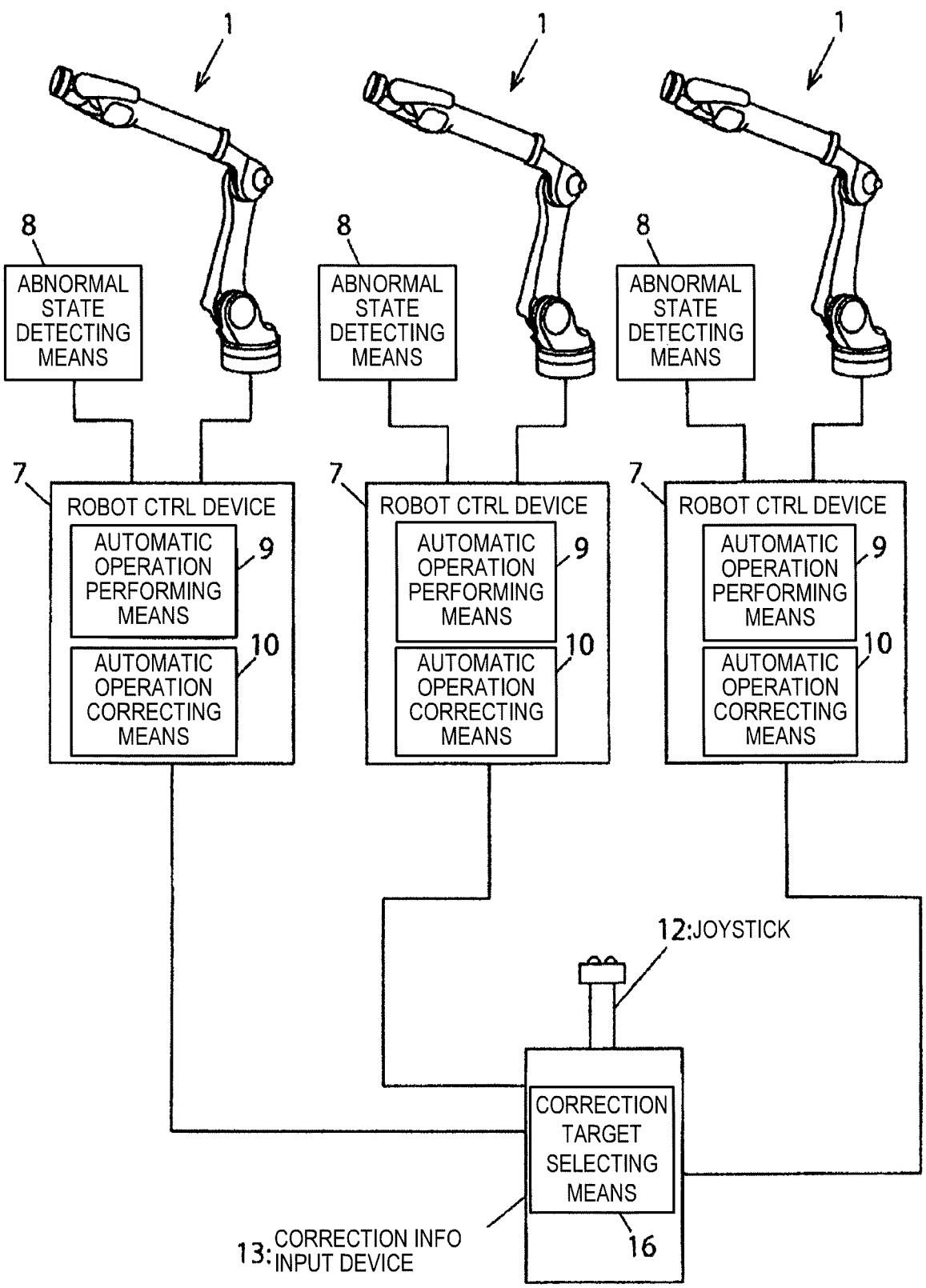
FIG. 6 is a schematic diagram illustrating a schematic configuration of an industrial robot according to one modification of the embodiment illustrated in FIG. 1.

Next, one modification of the embodiment described above will be described with reference to FIG. 6.

The industrial robot according to this example includes a plurality of robot main bodies 1 described above, and the robot control device 7 and the abnormal state detecting device 8 described above are provided to each robot main body 1.

Further, the correction information input device 13 includes a correction target selecting means 16 for selecting from the plurality of robot main bodies 1 the robot main body 1 of which operation is to be corrected by the automatic operation correcting means 10 described above.

In the industrial robot according to this example, an arbitrary one of the plurality of robot main bodies 1 is set to be a correction target, and it is operated in the operation correcting mode as needed. On the other hand, the remaining robot main bodies 1 are operated only in the automatic operation mode. Note that, the robot control device 7 may control the plurality of robot main bodies 1 by a single control device.

For example, the robot main body 1 performing the conveying operation of the workpiece W from the conveying source to the conveying destination only operates in the automatic operation mode, and the robot main body 1 performing the assembling operation of the workpiece W to the target object O at the conveying destination operates in the operation correcting mode as needed.

In this example, since it is possible to select the robot main body 1 as the correction target by using the correction target selecting means 16, simply providing a single correction information input device 13 for the plurality of robot main bodies 1 will suffice, and it is possible to prevent the structure from becoming complex.

For example, when performing the conveying operation for conveying the workpiece W from the conveying source to the conveying destination and the assembling operation for assembling the workpiece to the target object at the conveying destination, since the correction of the automatic operation is required mainly in the assembling operation, only the robot main body 1 performing the assembling operation may be set as the correction target.

[Second Modification]

Figure 7:
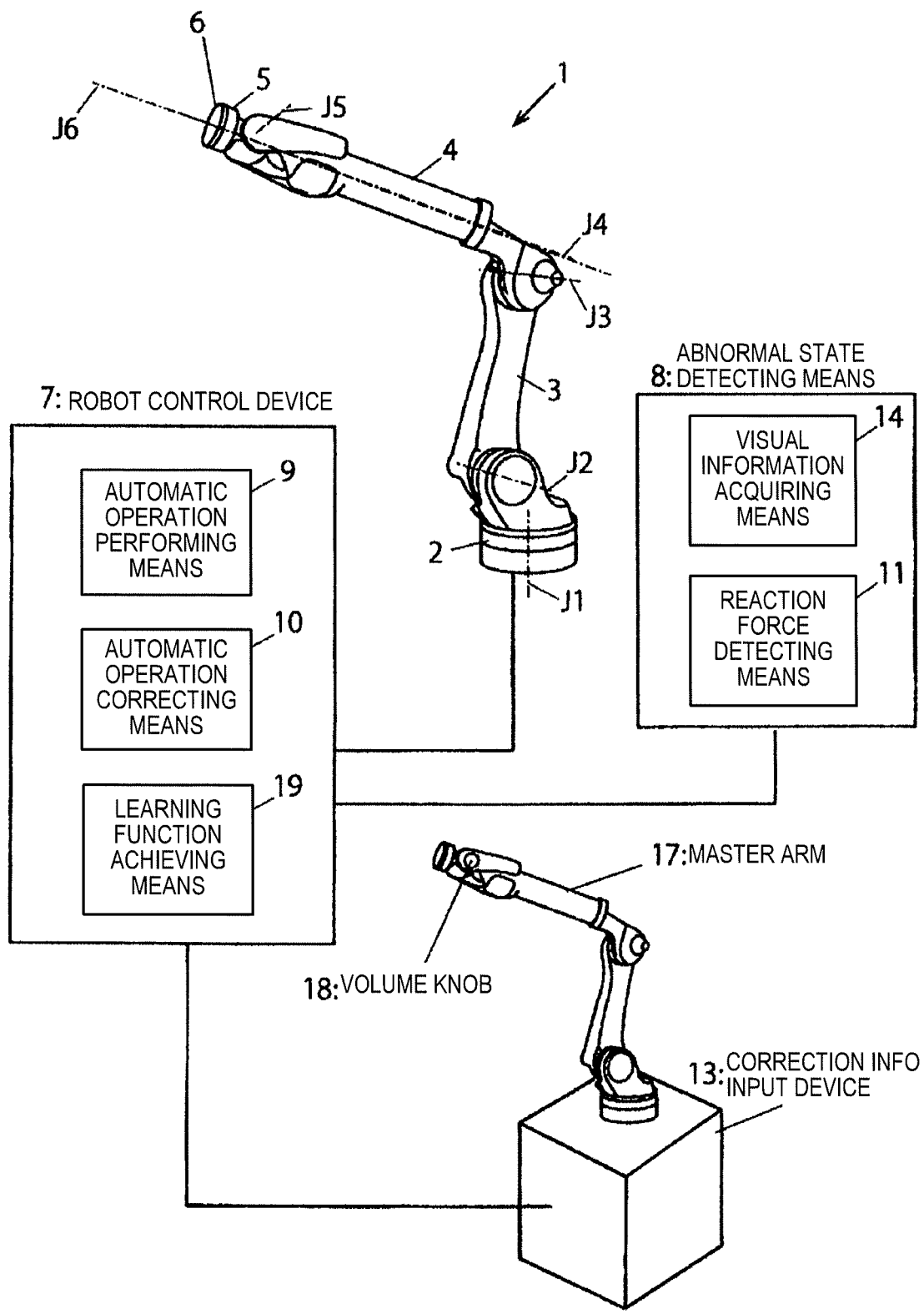
FIG. 7 is a schematic diagram illustrating a schematic configuration of an industrial robot according to another modification of the embodiment illustrated in FIG. 1.

Next, another modification of the embodiment described above will be described with reference to FIG. 7.

In this example, the correction information input device 13 includes a master arm 17 having a similar structure to the robot arm (slave arm) instead of the joystick.

The master arm 17 is provided with a volume knob 18 as the correction coefficient adjusting means described above, and the operator is able to adjust the correction coefficient $\alpha$ described above by manipulating this volume knob 18.

Further, in this example, the robot control device 7 includes the learning function achieving means 19 described above. It is possible to automatically correct the automatic operational instruction $\Delta P1$ described above by using the learning function achieving means 19, and the opportunities for the remote operator to intervene gradually decrease, and as a result, it is possible to achieve the assembling work only by the automatic operation.

Second Embodiment

[Configuration of Industrial Robot]

Figure 8:
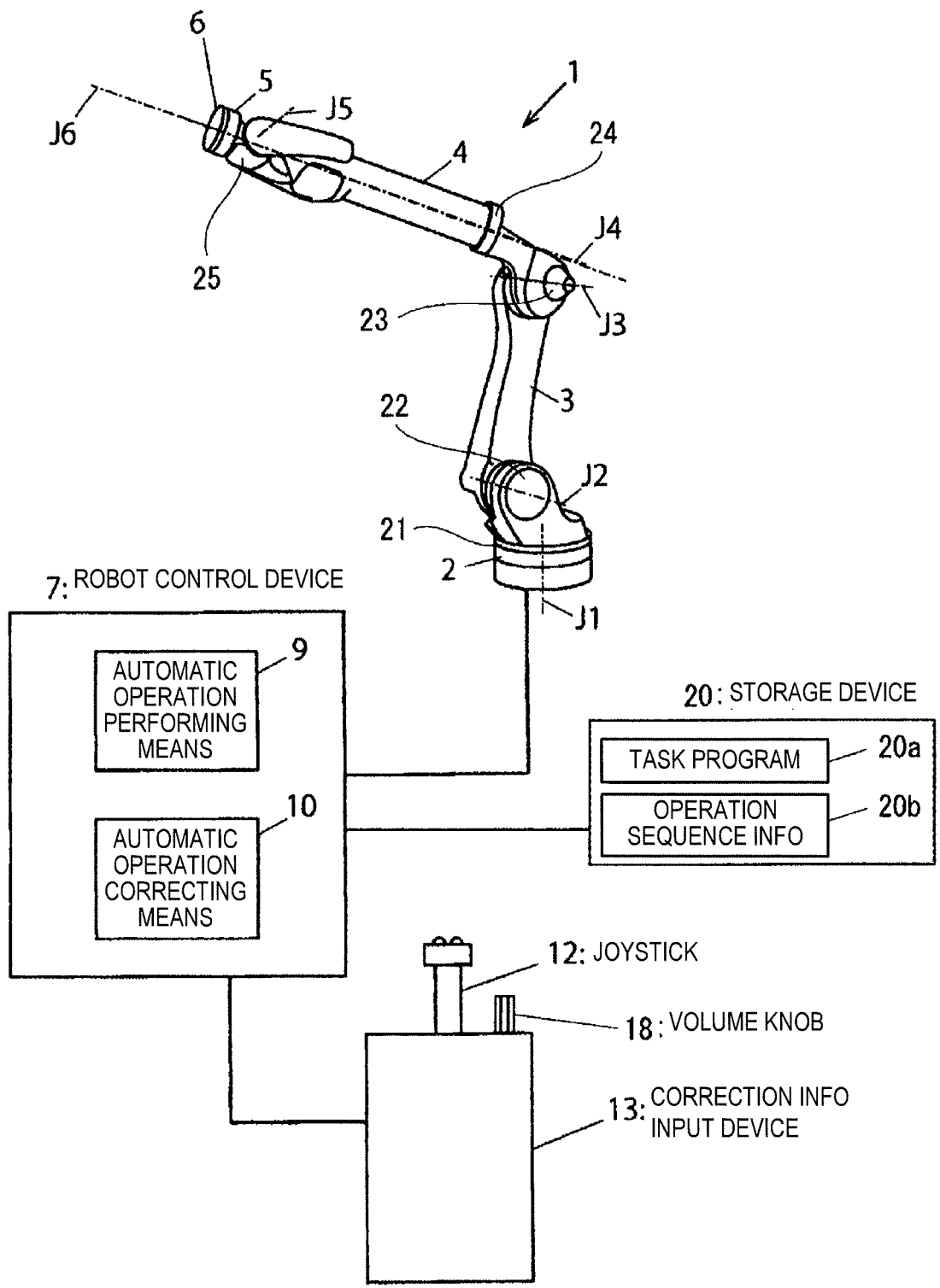
FIG. 8 is a block diagram illustrating a schematic configuration of an industrial robot according to a second embodiment.

FIG. 8 is a block diagram illustrating a schematic configuration of an industrial robot according to a second embodiment.

As illustrated in FIG. 8, although the industrial robot according to the second embodiment has the same basic configuration as the industrial robot according to the first embodiment, it is different in that the joystick 12 includes the volume knob (adjuster) 18. The volume knob 18 is configured to adjust a second coefficient B by the operator's manipulation.

Moreover, in the industrial robot according to the second embodiment, a storage device 20 is a readable and writable recording medium, which stores a task program 20*a* and operation sequence information 20*b* of the industrial robot. Note that, although in the industrial robot according to the second embodiment the storage device 20 is provided separately from the robot control device 7, it may be provided integrally with the robot control device 7.

The task program 20*a* is created by, for example, teaching and stored in the storage device 20 in association with identification information of the robot main body 1 and the task. Note that the task program 20*a* may be created as an operation flow for each work.

The operation sequence information 20*b* is information regarding an operation sequence which defines a series of work processes performed by the robot main body 1 in the workspace. In the operation sequence information 20*b*, an operation order of the work process and the control mode of the robot main body 1 are associated with each other. Further, in the operation sequence information 20*b*, a task program for causing the robot main body 1 to automatically execute the work is associated with each work process. Note that the operation sequence information 20*b* may include a program for causing the robot main body 1 to automatically execute the work for each work process.

Although the industrial robot according to the second embodiment adopts the form including the joystick 12, the present disclosure is not limited to this, and a form including the master arm 17 may be adopted instead of the joystick 12, or instead of the joystick 12, a form including a tablet type manipulator may be adopted.

[Operation and Effect of Industrial Robot]

Next, the operation and effects of the industrial robot according to the second embodiment will be described with reference to FIGS. 8 and 9.

Figure 9:
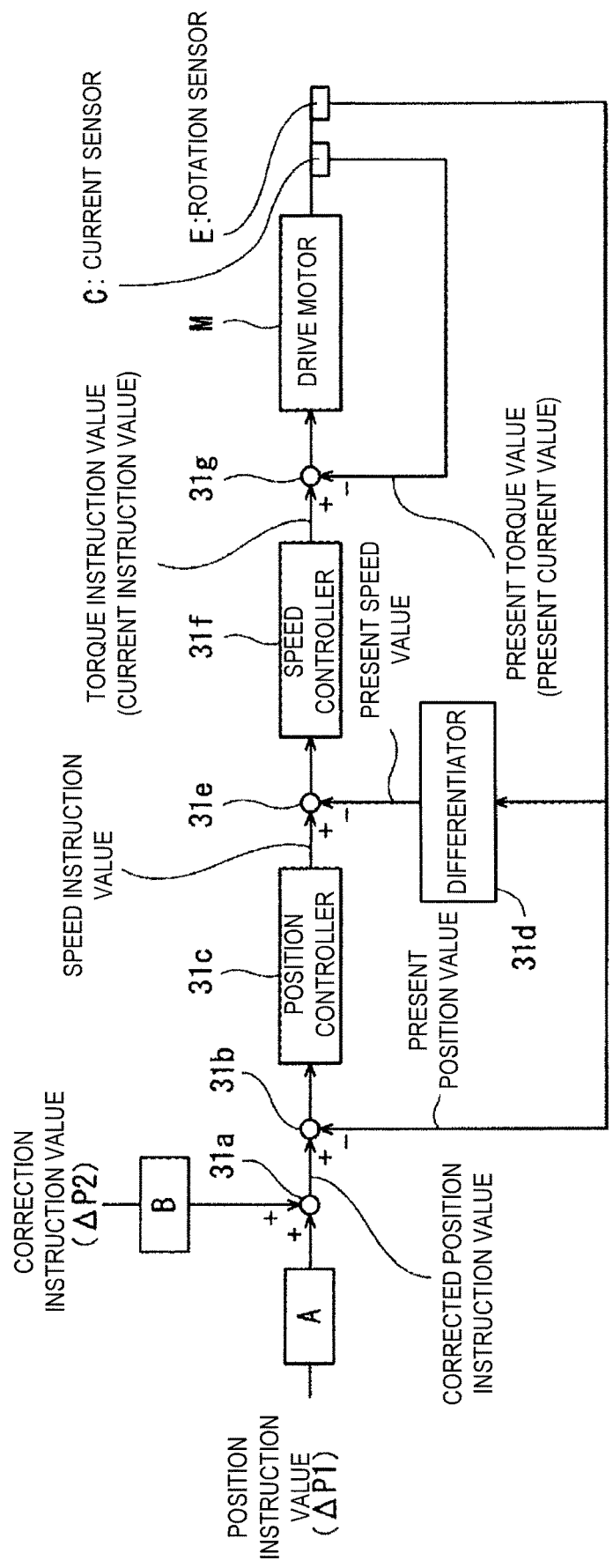
FIG. 9 is a block diagram illustrating one example of a control system of an automatic operation correcting means illustrated in FIG. 8.

FIG. 9 is a block diagram illustrating one example of a control system of an automatic operation correcting means illustrated in FIG. 8.

As illustrated in FIG. 9, the operation correcting mode executed by the automatic operation correcting means 10 of the industrial robot according to the second embodiment is executed basically similarly to the operation correcting mode executed by the automatic operation correcting means 10 of the industrial robot according to the first embodiment, except for the following point.

That is, in the industrial robot according to the second embodiment, the adder 31*a* of the automatic operation correcting means 10 generates the position instruction value according to the following Equation (2). Note that, since the operation after generating the position instruction value is executed similarly to the first embodiment, detailed description thereof is omitted.

$$\Delta P0 = A \times \Delta P1 + B \times \Delta P2 \quad \text{(Equation 2)}$$

Here, the first coefficient A and the second coefficient B are variables, and they are in a relationship in which when one of the coefficients increases, the other coefficient decreases. More specifically, the first coefficient A and the second coefficient B may be coefficients with which a value obtained by multiplying the first coefficient A and the second coefficient B becomes a first given preset value, or coefficients with which a value obtained by adding the first coefficient A and the second coefficient B becomes a second given preset value. Note that the first given value or the second given value may be 1, 10 or 100.

Note that, as described above, the second coefficient B may be inputted from the correction information input device 13 to the automatic operation correcting means 10 by the operator manually adjusting the volume knob (adjuster) 18 provided to the joystick 12. Further, as the adjuster, for example, a program for causing the second coefficient B to be 0 at a great distance from the work target (a structure to which a workpiece is attached, etc.), and is gradually increased as approaching the work target may be stored in advance in the storage device 20.

Moreover, the second coefficient B may be a variable which becomes, after a value is inputted from the volume knob 18 to the automatic operation correcting means 10 via the correction information input device 13, the inputted value over a given period of time, or a variable which becomes, after the correction instruction value $\Delta P2$ is inputted from the joystick 12 to the automatic operation correcting means 10, a preset value over a given period of time. For example, in view of preventing the correction of the operation of the robot main body 1 from being sharp, the given time may be 0.5 seconds or more, or may be 1 second or more. Further, in view of the operator acknowledging that the corrected operation of the robot main body 1 is reflected, the given time period may be within 2 seconds, within 3 seconds, or within 5 seconds.

More specifically, for example, the second coefficient B may be such a variable that a relationship between a lapsed period of time since the value is inputted from the volume knob 18 to the automatic operation correcting means 10 or the correction instruction value $\Delta P2$ is inputted from the volume knob 18 to the automatic operation correcting means 10 and a change amount $\Delta B$ per unit time corresponds to a linear function. Further, the second coefficient B may be such a variable that the relationship between the lapsed time period and the change amount ΔB per unit time corresponds to a high-dimensional function, such as a quadratic function or a cubic function, or it corresponds to a logarithmic function. Furthermore, the second coefficient B may be such a variable that the relationship between the lapsed time period and the change amount ΔB per unit time increases stepwise.

Thus, when the correction instruction value ΔP2 is inputted from the joystick 12 to the automatic operation correcting means 10, it is possible to prevent that the operation of the robot main body 1 is sharply corrected and the robot main body 1 is operated in an unexpected direction.

Even with the industrial robot according to the second embodiment configured as above, similar operations and effects to those of the industrial robot according to the first embodiment are obtained. Further, in the industrial robot according to the second embodiment, when the second coefficient B is the variable which becomes, after the value is inputted from the volume knob 18 to the automatic operation correcting means 10, the inputted value over the given period of time, or the variable which becomes, after the correction instruction value ΔP2 is inputted from the joystick 12 to the automatic operation correcting means 10, the preset value over the given period of time, it is possible to prevent that the operation of the robot main body 1 is sharply corrected and the robot main body 1 is operated in the unexpected direction.

Next, modifications of the industrial robot according to the second embodiment will be described.

[First Modification]

Figure 10:
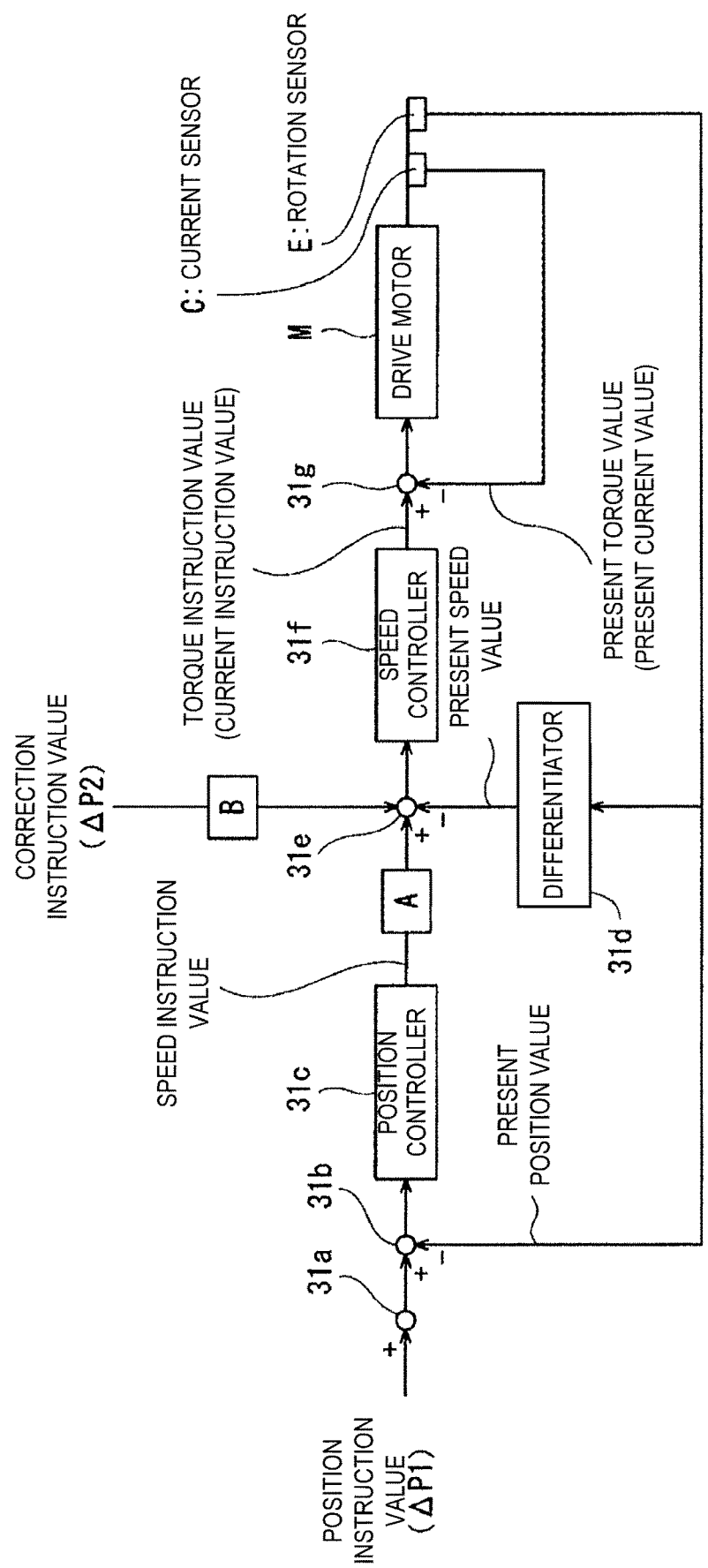
FIG. 10 is a block diagram illustrating one example of a control system of an automatic operation correcting means of an industrial robot according to a first modification of the second embodiment.

FIG. 10 is a block diagram illustrating one example of a control system of an automatic operation correcting means of an industrial robot according to a first modification of the second embodiment.

As illustrated in FIG. 10, in the first modification, operation performed by the automatic operation correcting means 10 when the correction instruction value ΔP2 inputted from the joystick 12 to the automatic operation correcting means 10 is the speed instruction value is described. This will be described in detail below.

When ΔP2 is the speed instruction value, a value obtained by multiplying the speed instruction value as ΔP2 (manual speed instruction value) by the second coefficient B is inputted to the subtractor 31e. Further, the subtractor 31e is supplied with a value which the position controller 31c obtains by multiplying the speed instruction value generated based on the operational instruction for the robot in the automatic operation (ΔP1; position instruction value) and the present position value, by the first coefficient A (corrected speed instruction value). Furthermore, the subtractor 31e is supplied with the present speed value generated by the differentiator 31d, from this differentiator 31d.

Then, the subtractor 31e adds the corrected speed instruction value to the inputted manual speed instruction value and generates the speed deviation based on the value obtained by subtracting the present speed value. Note that the operation after the subtractor 31e generates the speed deviation is executed in the similar manner to the industrial robot according to the first embodiment.

Even with the industrial robot according to the first modification, similar operations and effects to those of the industrial robot according to the second embodiment are obtained.

[Second Modification]

Figure 11:
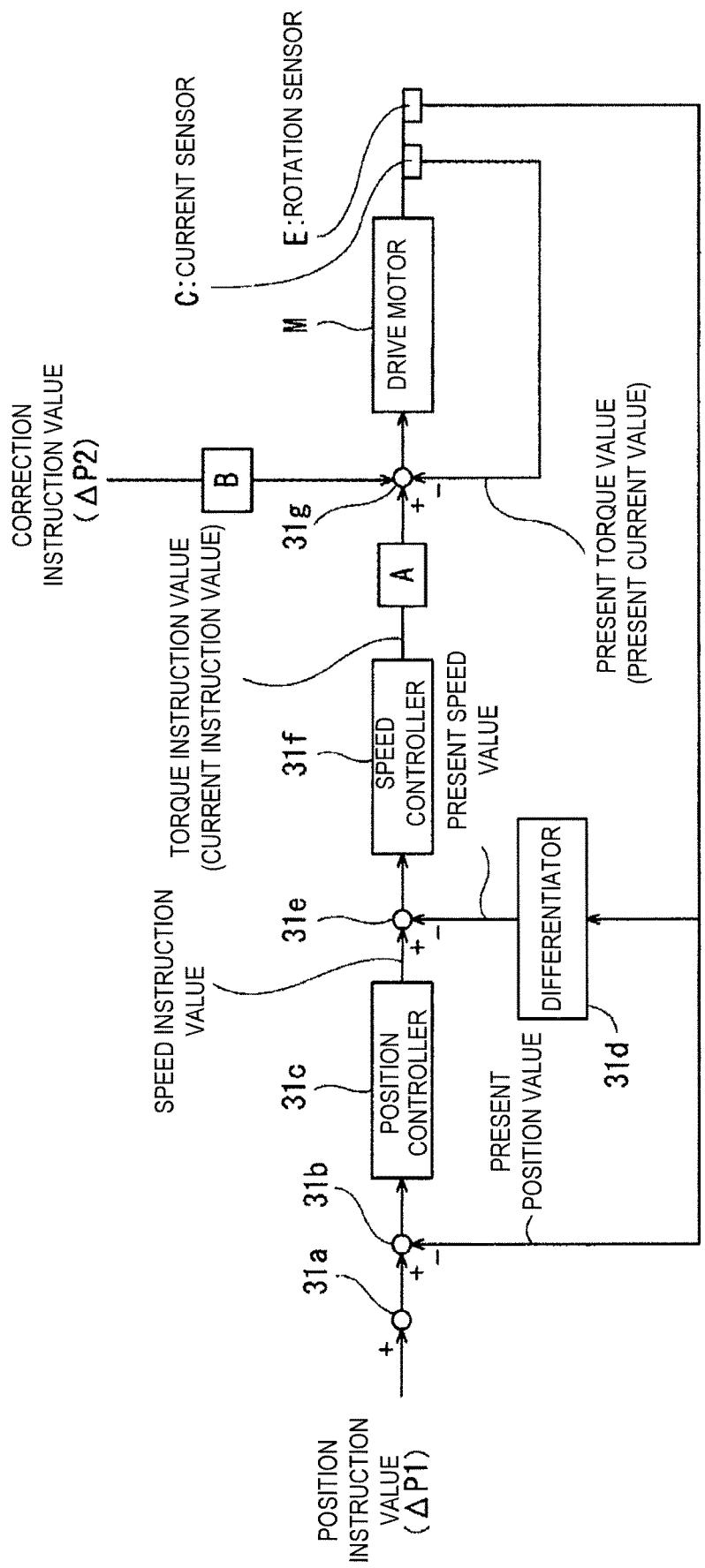
FIG. 11 is a block diagram illustrating one example of a control system of an automatic operation correcting means of an industrial robot according to a second modification of the second embodiment.

FIG. 11 is a block diagram illustrating one example of a control system of an automatic operation correcting means of an industrial robot according to a second modification of the second embodiment.

As illustrated in FIG. 11, the second modification describes the operation performed by the automatic operation correcting means 10 when the correction instruction value ΔP2 inputted from the joystick 12 to the automatic operation correcting means 10 is the torque instruction value. This will be described in detail below.

When ΔP2 is the torque instruction value, a value obtained by multiplying the torque instruction value as ΔP2 by the second coefficient B (manual torque instruction value) is inputted to the subtractor 31g. Further, the subtractor 31g is supplied with a value obtained by multiplying the torque instruction value generated by the speed controller 31f by the first coefficient A based on the speed deviation inputted from the speed controller 31f via the position controller 31c and the subtractor 31e in response to the operational instruction for the robot in the automatic operation (ΔP1; position instruction value) (corrected torque instruction value). Furthermore, the subtractor 31g is supplied with the present current value detected by the current sensor C.

Then, the subtractor 31g adds the corrected torque instruction value to the inputted manual torque instruction value and subtracts the present current value to generate current deviation. The subtractor 31g sends the generated current deviation to the drive motor M to drive the drive motor M.

Even with the industrial robot according to the second modification, similar operations and effects to those of the industrial robot according to the second embodiment are obtained.

Note that the industrial robots and the methods of operating the same according to the embodiments and modifications thereof described above are particularly suitable for when a human and a robot coexist and perform work, or when a person and a robot work in cooperation. For example, even when delicate positioning is required in the assembling work of the workpiece, the operator is able to intervene as needed to perform the work in the operation correcting mode, therefore it is possible to perform the assembling work of the workpiece without any difficulty.

From the above description, it is apparent for a person skilled in the art that many improvements and other embodiments of the present disclosure are possible. Therefore, the above description is to be interpreted only as illustration, and it is provided in order to teach a person skilled in the art the best mode in which the present disclosure is implemented. Details of the structures and/or functions of the present disclosure may be substantially changed without departing from the scope of the present disclosure. Further, it is possible to form various inventions by suitably combining a plurality of components disclosed in the above embodiments.

DESCRIPTION OF REFERENCE CHARACTERS

1 Robot Main Body
2 Pedestal (Robot Main Body)
3 Lower Arm (Robot Main Body)
4 Upper Arm (Robot Main Body)
5 Wrist Part (Robot Main Body)
6 Rotary Body (Robot Main Body)
7 Robot Control Device
8 Abnormal State Detecting Device 9 Automatic Operation Performing Means
10 Automatic Operation Correcting Means
11 Reaction Force Detecting Means
12 Joystick
13 Correction Information Input Device
14 Visual Information Acquiring Means
15 End Effector (Robot Main Body)
16 Correction Target Selecting Means
17 Master Arm
18 Volume Knob (Correction Coefficient Adjusting Means)
Learning Function Achieving Means
20 Storage Device
20a Task Program
20b Operation Sequence Information
21 First Joint Part
22 Second Joint Part
23 Third Joint Part
24 Fourth Joint Part
25 Fifth Joint Part
31a Adder
31b Subtractor
31c Position Controller
31d Differentiator
31e Subtractor
31f Speed Controller
31g Subtractor
J1 First Axis
J2 Second Axis
J3 Third Axis
J4 Fourth Axis
J5 Fifth Axis
J6 Sixth Axis
O Target Object
W Workpiece

The invention claimed is:

1. An industrial robot, comprising:
a robot main body having a robot arm;
a robot control device configured to control operation of the robot main body; and
an abnormal state detecting device configured to detect abnormality in a work state of the robot main body,
wherein the robot control device is configured to execute:
an automatic operation mode in which the robot main body performs an automatic operation in accordance with a preset task program,
a manual operation mode in which the robot main body operates based on a manual operation of the operator received by a manual control input device, without executing the preset task program, and
an operation correcting mode in which the robot main body performs the automatic operation in accordance with the preset task program, with a predetermined feature of the automatic operation being corrected by the manual operation of the operator received by the manual control input device, and
wherein the robot control device includes:
an automatic operation performing means for performing the automatic operation of the robot main body in accordance with the preset task program in the automatic operation mode; and
an automatic operation correcting means for correcting the automatic operation of the robot main body based on the manual operation of the operator in the operation correcting mode, according to a detection result of the abnormal state detecting device, with the proviso that when the abnormal state is resolved, the operation correcting mode is switched to the automatic operation mode.

2. The industrial robot of claim 1,
wherein an end effector configured to hold a workpiece is provided to the robot arm, and
wherein the preset task program causes the robot main body to perform
a conveying operation in which the workpiece held by the end effector is conveyed from a conveying source to a conveying destination, and
an assembling operation in which the workpiece is attached to a target object at the conveying destination.

3. The industrial robot of claim 2,
wherein the abnormal state detecting device detects abnormality in the work state of the robot main body in the assembling operation.

4. The industrial robot of claim 3,
wherein the abnormality in the work state of the robot main body includes occurrence of an unexpected assembling error in the assembling operation.

5. The industrial robot of claim 1,
wherein the abnormal state detecting device has a reaction force detecting means for detecting a reaction force externally acting on the robot main body, and
wherein haptics information corresponding to a detection result of the reaction force detecting means is provided to the operator manually operating the manual control input device in the operation correcting mode.

6. The industrial robot of claim 1,
wherein the abnormal state detecting device provides visual information regarding a workspace of the robot main body to the operator.

7. The industrial robot of claim 1,
wherein a plurality of robot main bodies are provided, and
wherein the industrial robot further comprises a correction target selecting means for selecting the robot main body of which operation is to be corrected in the operation correcting mode, from the plurality of robot main bodies.

8. The industrial robot of claim 1,
wherein, in the operation correcting mode, when an operational instruction for the robot main body according to the preset task program is $\Delta P1$, an operational instruction for the robot main body according to the manual operation of the operator is $\Delta P2$, and a correction coefficient is $\alpha$ ($0 \leq \alpha \leq 1$), the automatic operation correcting means is configured to generate an operational instruction $\Delta P0$ to be given to the robot main body based on the following equation:

$$\Delta P0 = (1-\alpha) \times \Delta P1 + \alpha \times \Delta P2.$$

9. The industrial robot of claim 8,
wherein the automatic operation correcting means has a correction coefficient adjusting means for adjusting the correction coefficient.

10. The industrial robot of claim 1,
wherein the robot control device has a learning function achieving means for correcting, in the operation correcting mode, the automatic operation of the robot main body based on the manual operation of the operator and based on a history of corrections made by the automatic operation correcting means.

11. An industrial robot, comprising:
a robot main body having a robot arm;
a manipulator configured to receive a manipulating instruction from an operator;
a storage device storing a preset task program for causing the robot main body to perform a given operation; and
a robot control device configured to control the operation of the robot main body,
wherein the robot control device is configured to execute:
an automatic operation mode in which the robot main body performs an automatic operation in accordance with the preset task program,
a manual operation mode in which the robot main body operates based on a manual operation of the operator received by the manipulator, without executing the preset task program, and
an operation correcting mode in which the robot main body performs the automatic operation in accordance with the preset task program, with a predetermined feature of the automatic operation being corrected by the manual operation of the operator received by the manipulator, and
wherein the robot control device includes:
an automatic operation performing means for performing the automatic operation of the robot main body in accordance with the preset task program in the automatic operation mode; and
an automatic operation correcting means for, in the operation correcting mode, when an operational instruction for the robot main body according to the preset task program is $\Delta P1$, and an operational instruction for the robot main body according to the manual operation of the operator is $\Delta P2$,
correcting the automatic operation of the robot main body by giving instructions corresponding to a sum of a value obtained by multiplying $\Delta P1$ by a first coefficient A and a value obtained by multiplying $\Delta P2$ by a second coefficient B, to the robot main body, with the proviso that
when an abnormal state of the robot main body is resolved, the operation correcting mode is switched to the automatic operation mode.

12. The industrial robot of claim 11,
wherein the first coefficient A and the second coefficient B are associated with each other so that when one of the coefficients increases, the other coefficient decreases.

13. The industrial robot of claim 11,
wherein the first coefficient A and the second coefficient B are such coefficients that a value obtained by multiplying the first coefficient A and the second coefficient B becomes a first given preset value.

14. The industrial robot of claim 11,
wherein the first coefficient A and the second coefficient B are such coefficients that a value obtained by adding the first coefficient A to the second coefficient B becomes a second given preset value.

15. The industrial robot of claim 11,
wherein the second coefficient B is a variable that becomes a preset value over a given period of time since the operational instruction for the robot main body according to the manual operation of the operator is inputted from the manipulator.

16. The industrial robot of claim 11, further comprising an adjusting means for adjusting the second coefficient B.

* * * * *